United States Patent
Isawa et al.

(10) Patent No.: US 9,589,343 B2
(45) Date of Patent: Mar. 7, 2017

(54) PATTERN MEASUREMENT DEVICE, EVALUATION METHOD OF POLYMER COMPOUNDS USED IN SELF-ASSEMBLY LITHOGRAPHY, AND COMPUTER PROGRAM

(71) Applicant: Hitachi High-Technologies Corporation, Minato-ku, Tokyo (JP)

(72) Inventors: Miki Isawa, Tokyo (JP); Kei Sakai, Tokyo (JP); Norio Hasegawa, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 28 days.

(21) Appl. No.: 14/422,603

(22) PCT Filed: Aug. 2, 2013

(86) PCT No.: PCT/JP2013/070960
§ 371 (c)(1),
(2) Date: Feb. 19, 2015

(87) PCT Pub. No.: WO2014/050305
PCT Pub. Date: Apr. 3, 2014

(65) Prior Publication Data
US 2015/0243008 A1    Aug. 27, 2015

(30) Foreign Application Priority Data

Sep. 27, 2012  (JP) .................................. 2012-213385

(51) Int. Cl.
*G06K 9/00* (2006.01)
*G21K 5/00* (2006.01)
(Continued)

(52) U.S. Cl.
CPC .............. *G06T 7/001* (2013.01); *G01B 15/00* (2013.01); *G01B 15/04* (2013.01);
(Continued)

(58) Field of Classification Search
CPC .............. G06K 9/0002; G06K 9/00026; G06K 9/00013; G06K 9/00067; G06K 9/00087;
(Continued)

(56) References Cited

U.S. PATENT DOCUMENTS 8,114,306 B2    2/2012  Cheng et al.
8,636,914 B2 *  1/2014  Nakamura ............ G03F 7/0002
                                                        216/41
(Continued)

FOREIGN PATENT DOCUMENTS

JP    2006-269710 A    10/2006
JP    2006-351888 A    12/2006
(Continued)

OTHER PUBLICATIONS

International Search Report (PCT/ISA/210) dated Oct. 15, 2013 with English translation (five pages).

Primary Examiner — Sheela C Chawan
(74) Attorney, Agent, or Firm — Crowell & Moring LLP

(57) ABSTRACT

The purpose of the present invention is to provide a pattern measurement device which evaluates quantitatively and with high precision random patterns such as finger print patterns. In order to fulfill this purpose, a pattern measurement device which measures the pattern on a sample on the basis of an image acquired by a charged particle beam is proposed which selectively extracts linear or linearly approximable parts of the pattern on the sample, and outputs at least one of the following: the measurement of the distance between the extracted parts, the ratio of said extracted parts in a prescribed region, and the length of said (Continued)

extracted parts. Further, as a more specific embodiment, a pattern measurement device is proposed which calculates a frequency depending on a distance value between extracted parts, and outputs, as a pattern distance, distance values for which said frequency fulfills a prescribed condition.

17 Claims, 9 Drawing Sheets

(51) Int. Cl.

| | | |
|---|---|---|
| H01L 21/31 | (2006.01) | |
| G06T 7/00 | (2006.01) | |
| G01B 15/00 | (2006.01) | |
| G01B 15/04 | (2006.01) | |
| G06T 7/60 | (2006.01) | |
| G01N 23/225 | (2006.01) | |
| G06K 9/46 | (2006.01) | |
| G06K 9/52 | (2006.01) | |
| G06K 9/62 | (2006.01) | |

(52) U.S. Cl.
CPC ........... *G01N 23/2251* (2013.01); *G06K 9/46* (2013.01); *G06K 9/52* (2013.01); *G06K 9/6201* (2013.01); *G06T 7/0004* (2013.01); *G06T 7/0081* (2013.01); *G06T 7/60* (2013.01); *G01N 2223/418* (2013.01); *G01N 2223/623* (2013.01); *G06K 2009/4666* (2013.01); *G06K 2009/6213* (2013.01)

(58) Field of Classification Search
CPC .......... G06K 9/52; G06K 9/6201; G06K 9/46; G06K 2009/6213; G06K 2009/4666; G06T 7/001; G06T 7/0081; G06T 7/0004; G06T 7/60; G01N 23/2251; G01B 15/00; G01B 15/04
USPC ........ 382/144, 125, 124; 716/51, 54, 55, 50, 716/111, 110, 100; 427/558, 457, 427, 427/532, 553, 557; 438/694, 689, 706, 438/735, 736, 780, 758, 778; 430/4, 5, 430/311, 325, 269, 322, 330, 328, 313; 700/90, 121, 95, 117; 216/22, 41, 49, 63, 216/58, 67; 378/1, 34, 35
See application file for complete search history.

(56) References Cited

U.S. PATENT DOCUMENTS

| | | | | |
|---|---|---|---|---|
| 8,712,190 | B2* | 4/2014 | Nakamura | A61B 5/117 382/115 |
| 2007/0023653 | A1 | 2/2007 | Toyoda et al. | |
| 2007/0125948 | A1 | 6/2007 | Choi et al. | |
| 2010/0195916 | A1* | 8/2010 | Blondiaux | G06K 19/086 382/209 |
| 2010/0295183 | A1 | 11/2010 | Sandhu et al. | |

FOREIGN PATENT DOCUMENTS

| | | |
|---|---|---|
| JP | 2007-155701 A | 6/2007 |
| JP | 2007-192594 A | 8/2007 |
| JP | 2010-269304 A | 12/2010 |
| JP | 2012-98240 A | 5/2012 |
| WO | WO 2010/135168 A2 | 11/2010 |

* cited by examiner 301  302  303

FIG.4
(a)
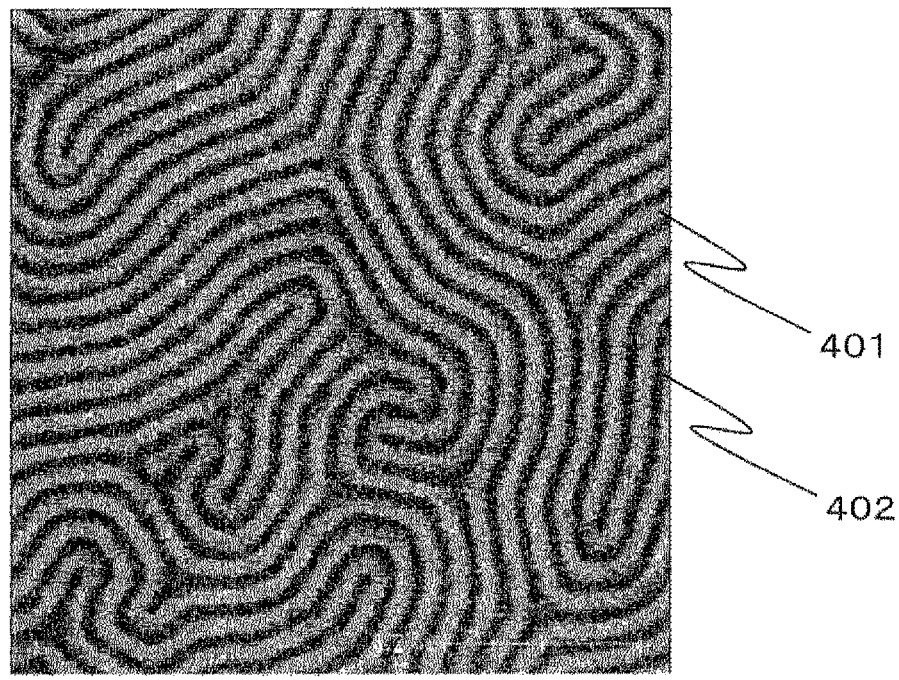
(b)
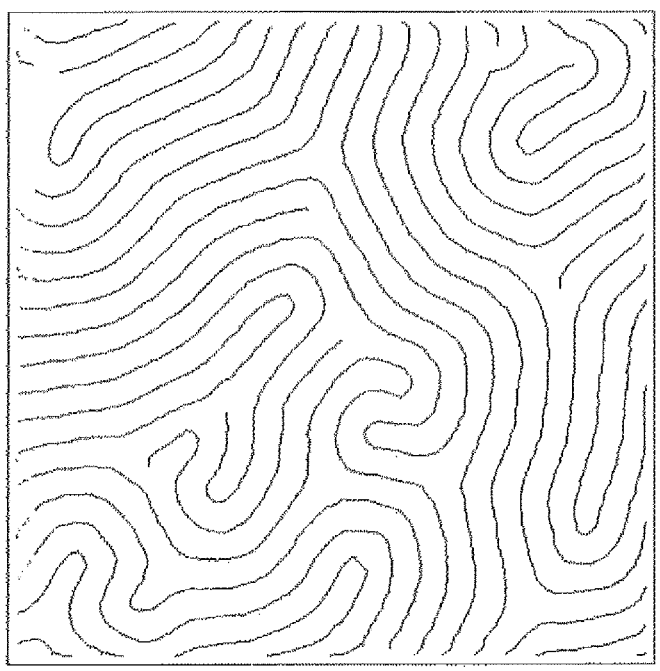

FIG.7
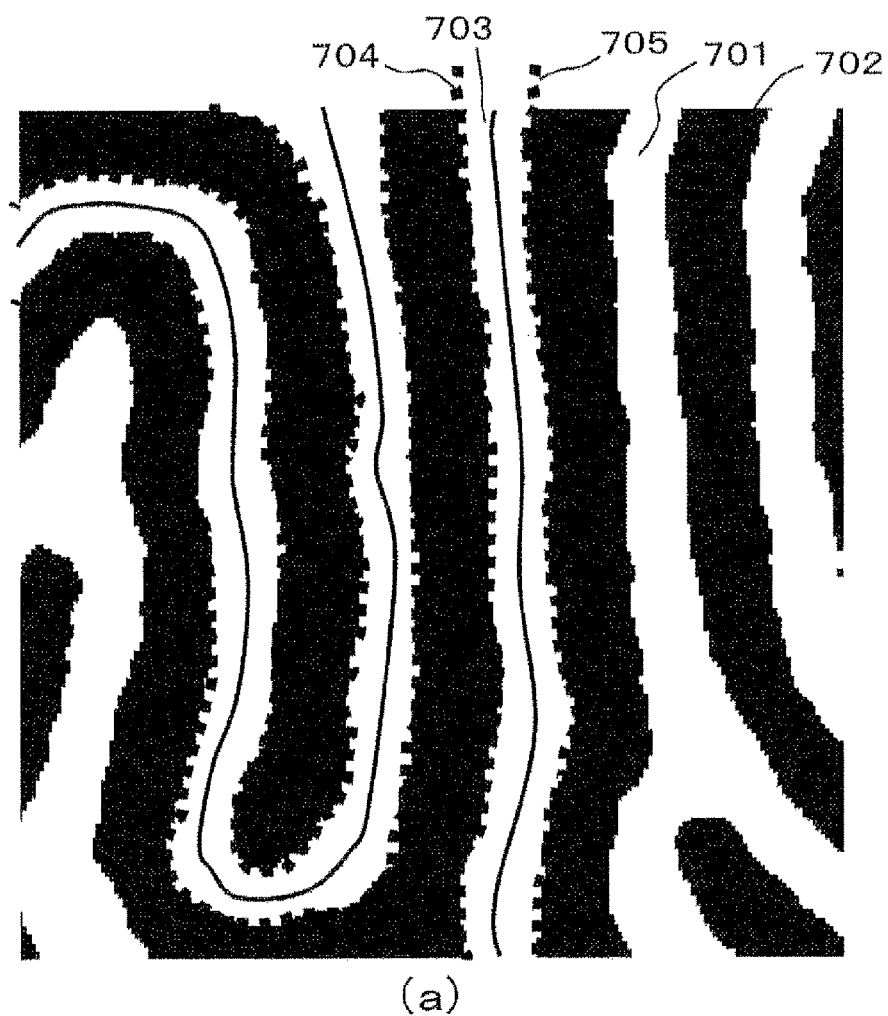
(a)
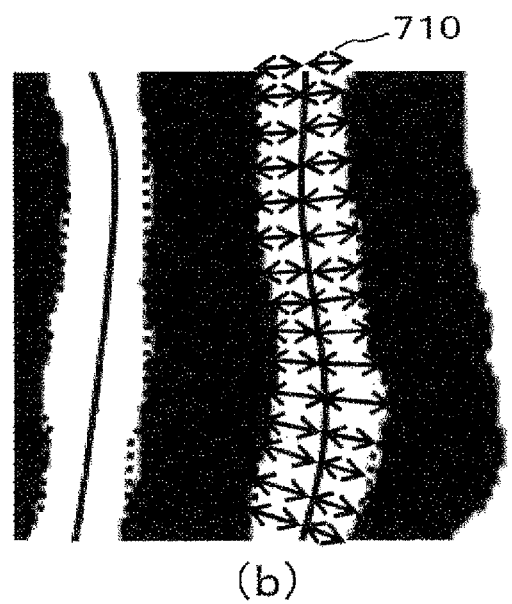
(b)

PATTERN MEASUREMENT DEVICE, EVALUATION METHOD OF POLYMER COMPOUNDS USED IN SELF-ASSEMBLY LITHOGRAPHY, AND COMPUTER PROGRAM

TECHNICAL FIELD

The present invention relates to a pattern measurement device which measures a pattern on the basis of information obtained by a charged particle beam device, and in particular to a pattern measurement device for measuring a random pattern such as polymers used in self-assembly lithography, an evaluation method, a computer program, and a storage medium capable of storing the computer program.

BACKGROUND ART

With recent advance of integration of semiconductor patterns, evaluation of workmanship in manufacture processes and research and development processes is becoming more important. On the other hand, DSA (Directed Self Assembly) technique attracts attention as a technique that makes it possible to shrink sizes of semiconductor patterns. The DSA is a new patterning technique utilizing the self-assembly phenomenon of polymers. The DSA is a technique employing a micro phase separation phenomenon in which macromolecular BCP (block copolymer) forms regular domains of nanometer-size. The shape and size of a pattern can be controlled by designing a molecular structure and a molecular weight of the BCP.

Since special devices or facilities are not used, it is possible to save the cost. In recent years, development of a semiconductor manufacture process using this method has been promoted. By coating the top of a substrate with BCP and applying thermal annealing, the BCP conducts self-assembly and conducts phase separation to a peculiar shape. For applying the BCP to actual semiconductor manufacture, it is necessary to cause the BCP to self-assemble to a desired shape. Therefore, it is necessary to control and induce the self-assembly phenomenon chemically or physically.

Patent Literature 1 describes an example of observing a pattern formed by the DSA technique with a scanning electron microscope and an example of conducting dimension measurement of a pattern.

CITATION LIST

Patent Literature

Patent Literature 1: JP-A-2010-269304 (corresponding U.S. Pat. No. 8,114,306)

SUMMARY OF INVENTION

Technical Problem

The greatest feature of patterning using the DSA is that the pitch and dimension of a pattern are determined by a material. In other words, the workmanship of a pattern depends upon to what degree the material can be manufactured according to specifications. Therefore, it is desirable to conduct one-hundred percent inspection every shipment. Furthermore, it is expected that an evaluation device capable of evaluating a material simply and with high precision will be demanded.

As an evaluation technique of a BCP material, a method of preparing a guide pattern for arranging the BCP material in a desired shape on a substrate beforehand, arranging the BCP material along the guide pattern, and thereafter conducting evaluation, and a method of coating the top of a substrate neutralized without using a guide pattern, with a BCP material and evaluating workmanship as a fingerprint pattern are conceivable. In a case where a guide pattern is used, the BCP material is arranged in a desired shape, and consequently quantification of the shape can be conducted simply. On the other hand, since workmanship of the guide pattern exerts an influence upon the BCP pattern, a case where pure material evaluation is not conducted is conceivable.

In the case of evaluation using the fingerprint, there is no influence of a guide pattern and consequently pure evaluation of the material is possible. Since there are curves and undulation of a pattern peculiar to the fingerprint, however, quantification is difficult with a simple method. Even if pitch measurement using Fourier analysis is conducted, these kinds of unnecessary information are included, resulting in lowered precision. Any evaluation method for evaluating the fingerprint pattern itself is not discussed at all in Patent Literature 1.

Hereafter, a pattern measurement device, method, and computer program aiming at evaluating a random pattern such as a fingerprint pattern quantitatively and with high precision.

Solution to Problem

As one aspect for achieving the object, the present inventors propose a pattern measurement device that measures a pattern on a sample on the basis of an image acquired by a charged particle beam, and that selectively extracts straight line portions of a pattern on the sample or portions which can be approximated by a straight line, and outputs at least one of measurement of a distance between the extracted portions, a ratio of the extracted portions in a predetermined region, and lengths of the extracted portions, and a computer program which causes a computer to execute the arithmetic operation.

Furthermore, as a more concrete aspect, the present inventors propose a pattern measurement device that finds a frequency depending upon a distance value between extracted portions and outputs a distance value at which the frequency satisfies a predetermined condition as a pattern distance, and a computer program which causes a computer to execute the output.

In addition, as another aspect for achieving the object, the present inventors propose a pattern evaluation method for evaluating a polymer used in self-assembly lithography, including selectively extracting straight line portions of patterns or portions that can be approximated with a straight line from within a fingerprint pattern image obtained by a charged particle beam device, and finding at least one of measurement of a distance between the extracted portions, a ratio of the extracted portions in a predetermined region, and lengths of the extracted portions.

Furthermore, the present inventors propose a pattern measurement device that finds center lines of a pattern on a sample, and executes measurement of variations on the basis of measurement of a distance between the center lines, or measurement of distances at a plurality of places between a center line and edges adjacent to the center line, or distances between edges on both sides with a center line between.

Advantageous Effects of Invention

According to the above-described configuration, it becomes possible to evaluate a random pattern such as a fingerprint pattern quantitatively and with high precision.

BRIEF DESCRIPTION OF DRAWINGS

FIGS. 4A and 4B are diagrams showing an SEM image of a fingerprint pattern, and an example of a contour line image obtained by extracting center lines of the pattern with respect to the SEM image;

FIGS. 7A and 7B are diagrams showing an example of evaluation of roughness of a fingerprint pattern;

DESCRIPTION OF EMBODIMENTS

Embodiments described hereafter mainly relate to a patterning measurement method and a measurement device in a patterning technique utilizing micro phase separation of block copolymer including two kinds of polymer.

With the size shrinking of semiconductor, it is becoming impossible for patterning using simple lithography to cope with the size shrinking. As a technique for prolonging the life of lithography, methods such as the multiple patterning method in which lithography processes of a plurality of times are combined and a nano imprint technique have been conceived. From the viewpoint of cost and implementation possibility, however, any method has not made a decisive hit. The present embodiment relates to a device, method, and computer program for properly evaluating polymers used in the DSA technique anticipated as an effective patterning technique, and relates to a storage medium capable of storing the computer program.

In the present embodiment, evaluation is conducted by using only a portion of a fingerprint pattern where the pattern forms a straight line in order to improve the precision of evaluation using the fingerprint pattern. As a result, quantification of a shape with high precision using only a straight line portion without being affected by the workmanship of a guide patter becomes possible. Specifically, when acquiring an image of a fingerprint pattern and conducting image processing, a curved portion is masked and evaluation is conducted by using only a straight line portion. Hereafter, an evaluation method of the fingerprint pattern will be described in detail with reference to the drawings.

Figure 1:
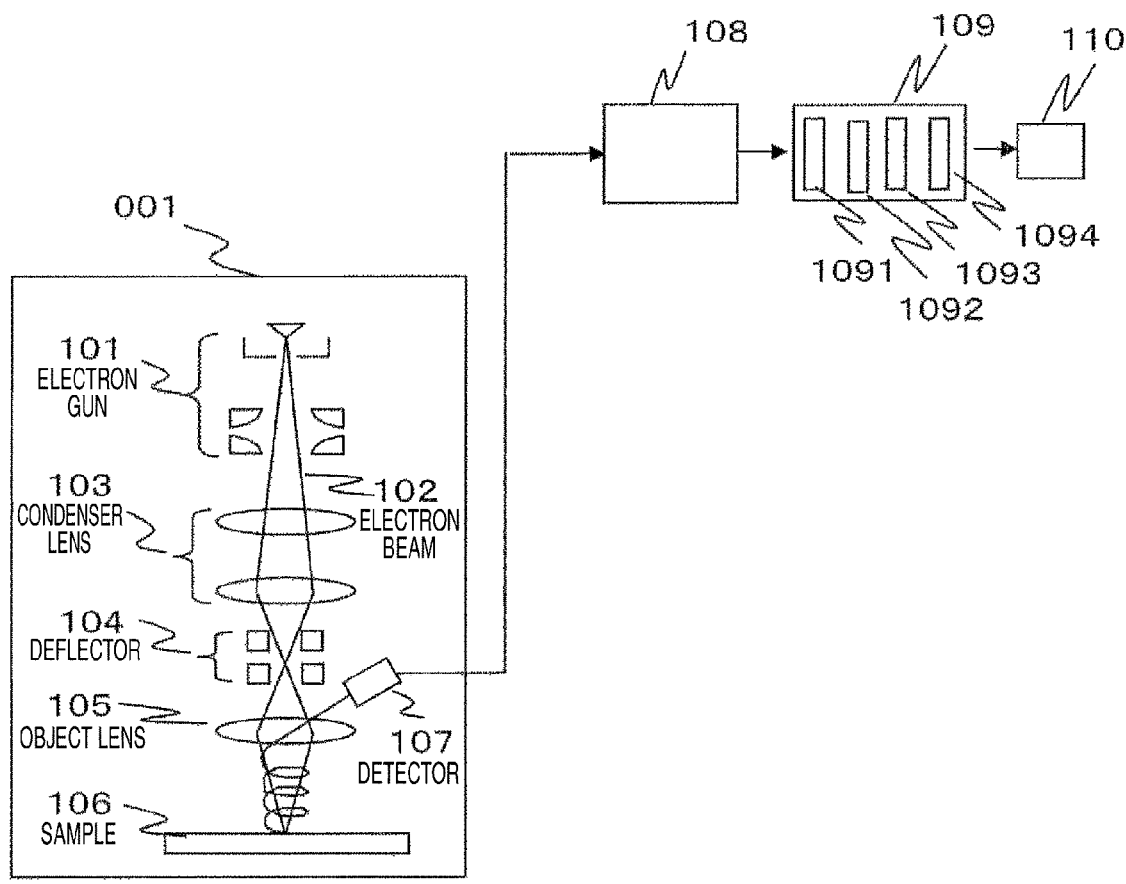
FIG. 1 is a diagram showing an outline of a scanning electron microscope.

A pattern measurement method will now be described. In an SEM 001 shown in FIG. 1, an SEM image of a sample is acquired under previously set imaging conditions (such as a magnification and an acceleration voltage of an irradiation beam). Specifically, an electron beam 102 emitted from an electron gun 101 in the SEM 001 is converged by a condenser lens 103. Scanning in an X direction and a Y direction (in a plane perpendicular to the drawing in FIG. 1) with the electron beam is conducted by a deflector 104. The electron beam is focused on a surface of a sample 106 with a measurement target pattern formed thereon, by an object lens 105. The surface of the sample 106 is scanned and irradiated with the electron beam. Although illustration is omitted in FIG. 1(a), the sample 106 is placed on a table and is capable of moving in the plane. Control is exercised to position a desired area on the surface of the sample 106 in an area irradiated with the electron beam 102. A portion of secondary electrons generated from the surface of the sample 106 irradiated with the electron beam 102 is detected by a detector 107, and converted to an electric signal. The electric signal is sent to a general control & image processing unit 108, and an SEM image is created. In an arithmetic operation unit 109, the SEM image is processed and dimensions of the pattern are calculated. Results are displayed on a screen in an output unit 110. The general control & image processing unit 108 exercises control of the whole SEM 001 including the table on which the sample 106 is placed and which is not illustrated.

Figure 2:
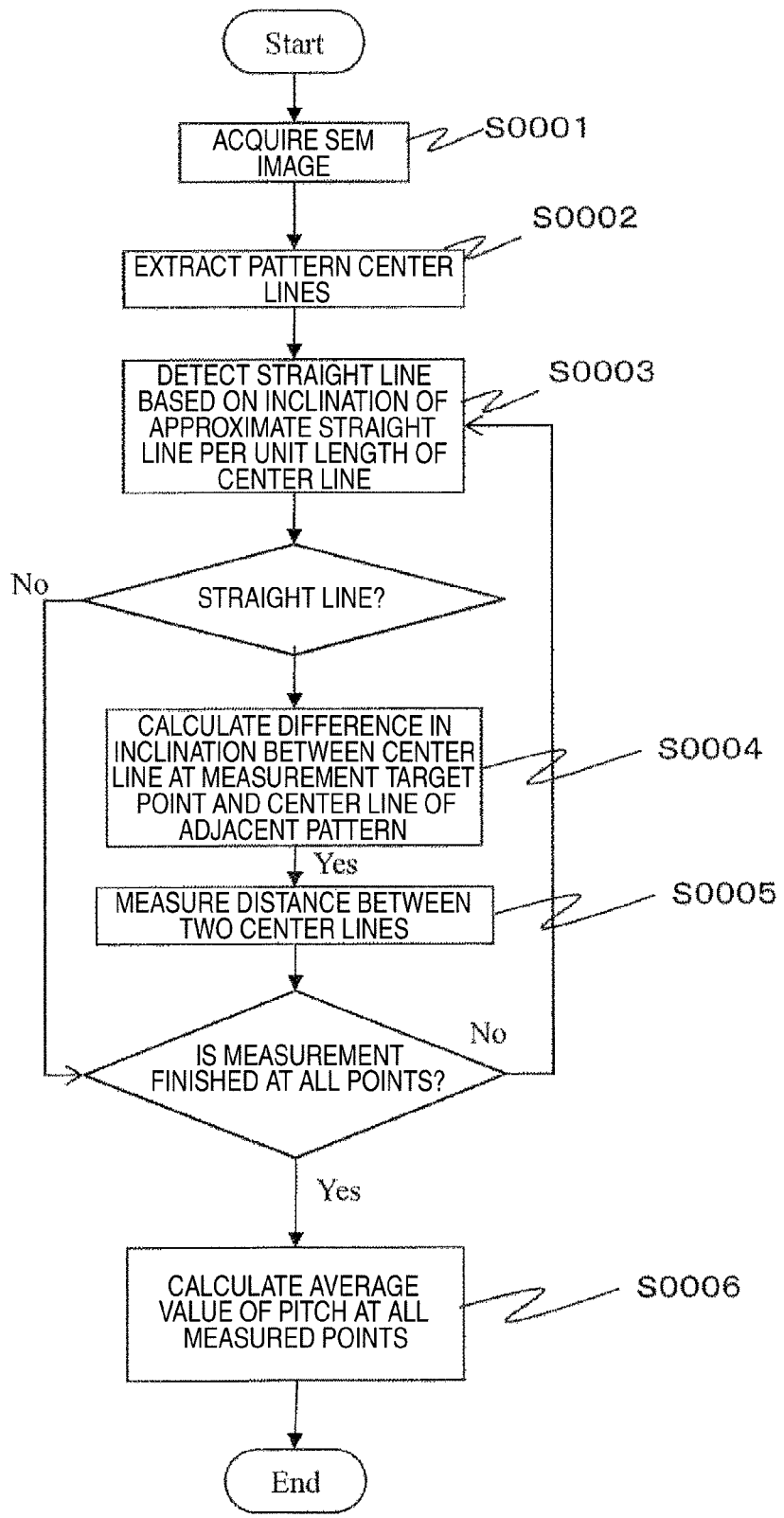
FIG. 2 is a flow chart showing a measurement process of a fingerprint pattern.

A processing procedure in the arithmetic operation unit 109 is shown in FIG. 2. First, as described above, the general control & image processing unit 108 controls the SEM 001 and acquires an SEM image of a measurement target pattern (S0001). Then, the arithmetic operation unit receives the SEM image acquired by the general control & image processing unit 108, processes the SEM image, and conducts extraction of pattern center lines (S0002). Details of measurement at the step (S0002) will be described later.

Then, at step (S0003), a decision as to the linearity of a center line is conducted on the basis of inclination of the center line per unit length. In a case where it is confirmed that an area is a straight line area as a result of this decision, inclinations of two center lines are compared at next step (S0004), and a distance is measured only in parallel portions (S0005). This processing is conducted for all measurement points which are set in the image. After measurement is conducted at all points, an average measured value is calculated at step (S0006). As a result, an inherent pitch of the BCP material is found. An extracted center line is displayed to be superposed on the SEM image on the GUI.

By the way, in the present embodiment, a device in which a computer including an image processing processor (decision unit) that conducts quantification of a finger print pattern shape described hereafter on the basis of a signal of secondary electrons or the like is included as a portion of a scanning electron microscope device is exemplified as an example of a pattern measurement device. However, the pattern measurement device is not restricted to the exemplified device. For example, an external measurement device including an interface for acquiring information (such as a secondary electron signal, signal waveform information based on detection of secondary electrons, a two-dimensional image signal, or contour line information of pattern edges extracted from the image) based on a signal acquired by the scanning electron microscope, and an arithmetic operation device corresponding to the above-described image processing processor may conduct quantification of a pattern shape described later. It is also possible to previously register a program which conducts processing described later into a storage medium and cause a processor which supplies a necessary signal to a scanning electron microscope or the like to execute the program. In other words, the ensuing description is also description of a program or a program product which can be executed in a pattern measurement device such as a scanning electron microscope.

By the way, the scanning electron microscope using an electron beam has been described heretofore as an example of the charged particle beam device. However, the charged particle beam device is not restricted to the scanning electron microscope using an electron beam. For example, the charged particle beam device may be an ion beam irradiation device using an ion beam.

Figure 8:
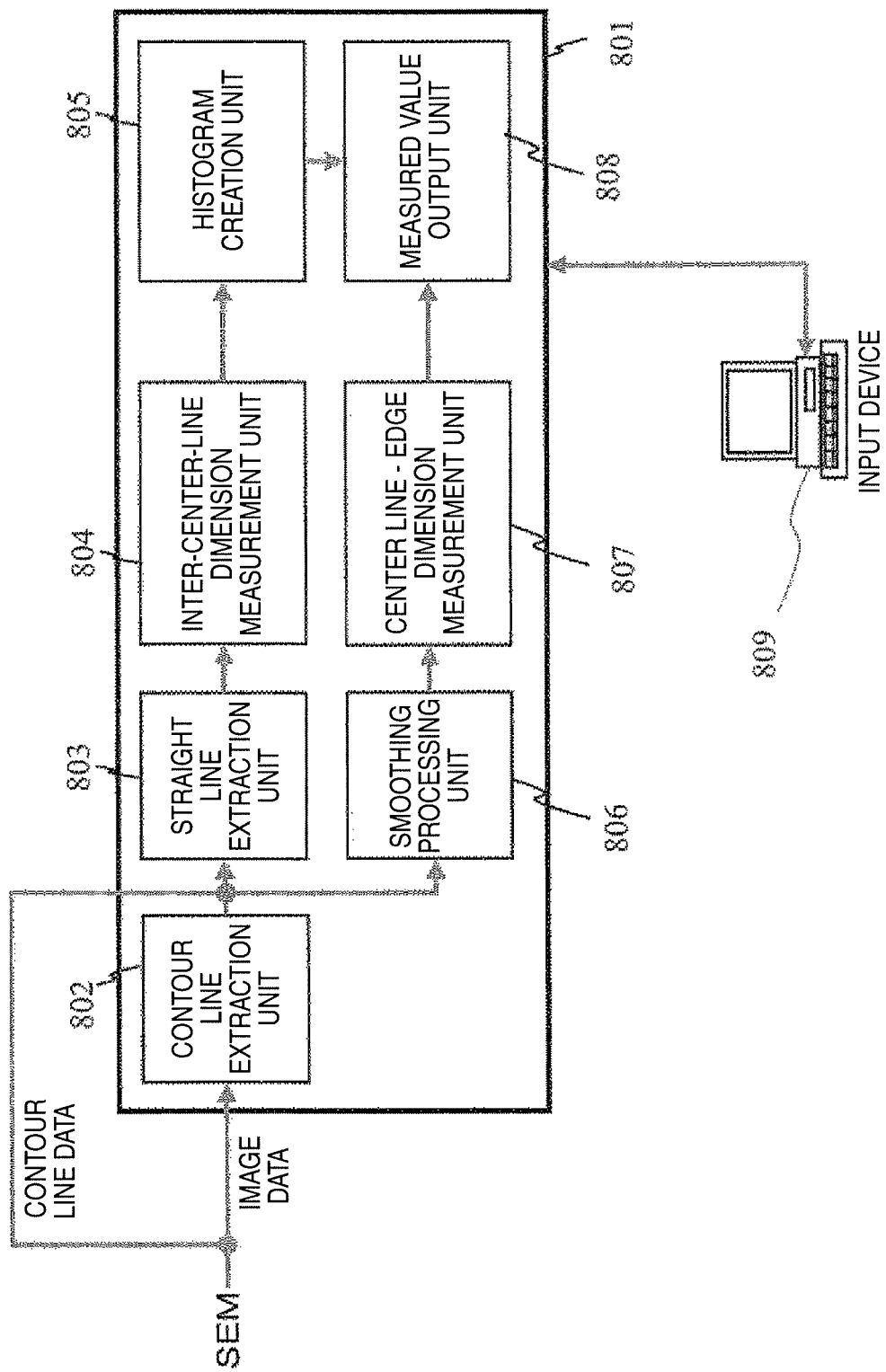
FIG. 8 is a diagram showing an outline of a pattern measurement device which executes pattern measurement by using image information obtained by a scanning electron microscope.

FIG. 8 is a diagram showing an example of a pattern measurement device which executes pattern measurement by using image information obtained by a scanning electron microscope. A pattern measurement device 801 is an arithmetic operation device which executes various kinds of processing along a previously stored program. The pattern measurement device 801 includes a contour line extraction unit 802 which extracts contour lines from image data output in the SEM 001 exemplified in FIG. 1. By the way, in a case where a contour line extraction unit is mounted on the SEM 001, this function can be omitted. As for the extracted contour lines, a straight line portion is selectively extracted by a straight line portion extraction unit 803. An inter-center-line dimension measurement unit 804 measures a distance (pitch) between center lines of a pattern on the basis of the extracted straight line portion as described later. A histogram creation unit 805 finds a frequency of each measurement result as regards results of measurement conducted by the inter-center-line dimension measurement unit 804, and creates a histogram. A measured value output unit 808 outputs a measurement result of a specific frequency to a display device in, for example, an input device 809.

Furthermore, the pattern measurement device 901 can function as a roughness measurement device as well. In a case where the pattern measurement device functions as a roughness measurement device, first, a smoothing processing unit 806 conducts smoothing processing on the obtained image data and contour line data, a center line-edge dimension measurement unit 807 measures a plurality of dimensions between edges of a pattern and center lines of the pattern subjected to the smoothing processing, and the measurement value output unit 808 outputs results of the measurement to the display device or the like. Operation of the pattern measurement device 801 will be further described.

Figure 9:
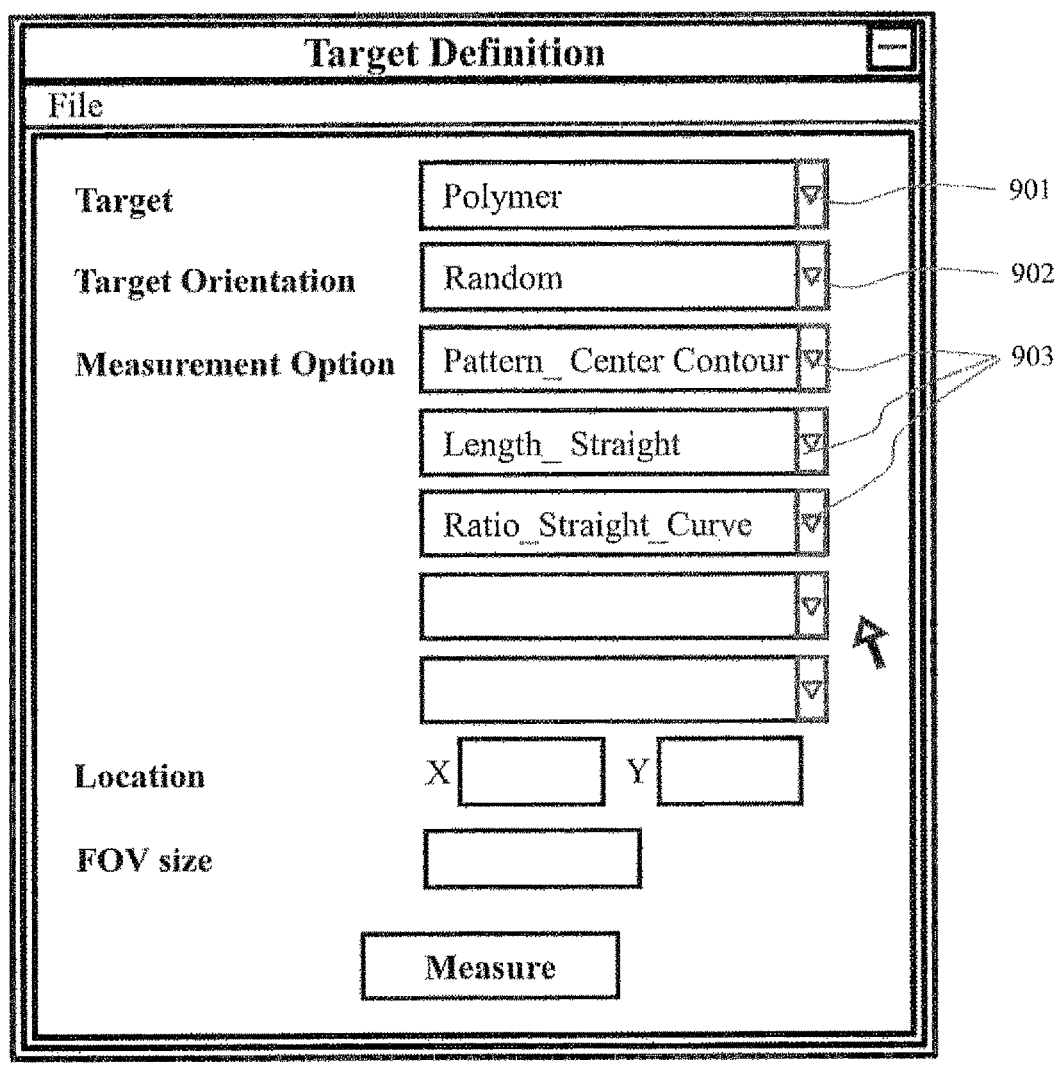
FIG. 9 is a diagram showing an example of a GUI (Graphical User Interface) screen for setting measurement conditions.

FIG. 9 is a diagram showing an example of a GUI screen for setting conditions of measurement conducted by the scanning electron microscope. It becomes possible for an operator to select proper conditions along a measurement target by displaying such a GUI on the display device in, for example, the input device 809. In the GUI exemplified in FIG. 9, a window 901 for selecting a kind of a measurement object (target) is provided. In the example in FIG. 9, Polymer is selected. Furthermore, a window 902 for inputting Target Orientation (direction of the target) is provided, and Random is selected in the example in FIG. 9. In the present example, selection contents in a measurement item selection window (Measurement Option) 903 change on the basis of inputs to the windows 901 and 902. For example, if Line (line pattern) and Vertical are selected respectively in windows 901 and 902, the measurement target is a line pattern which is long in a longitudinal direction, and consequently it becomes possible to select measurement items suitable for the line pattern, such as measurement of a dimension between line edges and measurement of a line pitch, in the window 903.

As for a polymer selected in the example in FIG. 9, an edge peak does not appear unlike an ordinary wiring pattern. Therefore, it becomes possible to select measurement items for extracting center lines of the pattern in the whole image and then finding distances between the center lines by selecting, for example, (Pattern Center Contour). Furthermore, an example in which a length of a straight line portion (Length Straight) and a ratio of a straight line portion to a curve portion in the pattern (Ratio Straight Curve) are selected is shown in FIG. 9. Contents of these measurement items will be described later. Besides, it becomes possible to execute measurement based upon selection of a suitable operation program by selecting coordinates (Location) of a measurement target, a field of vision size (FOV size) and so forth and transmitting these measurement conditions to the SEM or the pattern measurement device 801.

Hereafter, an outline of a fingerprint pattern which is a measurement target in the present embodiment of the scanning electron microscope will be described.

Figure 3:
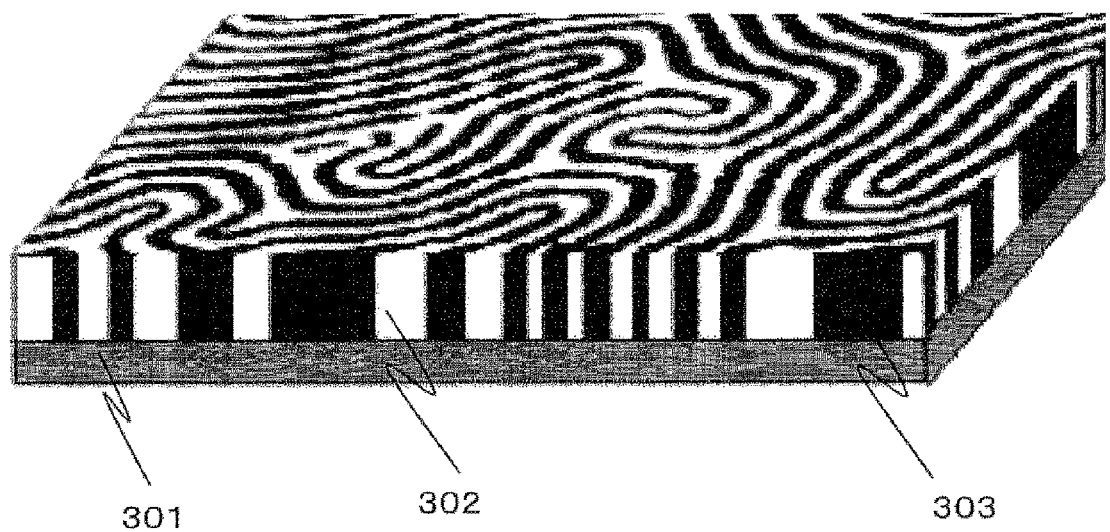
FIG. 3 is an outline diagram of a fingerprint pattern.

FIG. 3 shows an outline of a fingerprint pattern. The fingerprint pattern takes a structure in which a pattern formed by two kinds of polymer (referred to as A and B) stands erect on a substrate 301 and polymer A 302 and polymer B 303 are arranged alternately in a fingerprint form. In lithography using the Directed-Self-Assembly technique, compositions (such as molecular weights, molecular chain lengths, and a separation degree between the two kinds of polymer) of polymers in use and their variations affect workmanship of the pattern shape. When introducing a new material or process, therefore, it is necessary to evaluate the workmanship of polymers as materials and confirm patterning capability. The fingerprint pattern is used at that time. The fingerprint pattern is obtained by neutralizing a Si substrate, then coating the Si substrate with polymers having self-assembly capability, and conducting anneal processing at a determinate temperature. The shape (such as a line width, pitch, curvature of a curved place, and a length of a straight line portion) of the fingerprint pattern differs depending upon the material, and the shape becomes a clue to material evaluation.

Hereafter, a quantification technique of the pattern shape based on an image will be described. An SEM image shown in FIG. 4(a) is an image obtained by observing the pattern provided with a difference in level between the two kinds of polymer by selectively etching one of the polymers after the annealing. At this time in the image, a difference in polymer appears as a difference in luminance. Hereafter, a portion 401 having a high luminance in the image is referred to as polymer A, and a portion 402 having a low luminance in the image is referred to as polymer B.

The pitch of repetition of the polymer A and the polymer B is inherent depending upon the configuration (molecular weights respectively of the polymer A and the polymer B, or composition of additives) of the BCP material. Therefore, it can be determined whether the BCP material has a composition as designed, by measuring a pattern pitch (a distance between center lines). By the way, in the fingerprint pattern after the annealing, there is no difference in level between the two kinds of polymer. In the SEM, therefore, it is difficult to obtain a contrast in some cases. At that time, an image may be picked up after the visibility of the pattern in the SEM is improved by conducting etching after the annealing. Furthermore, irradiation with the electron beam conducted by the SEM functions to contract one polymer in some cases. At that time, irradiation with the electron beam should be conducted before image pickup, and an image for evaluation should be acquired after the visibility is improved.

Hereafter, a technique of measuring the pattern pitch will be described. First, the SEM 001 or the contour line extraction unit 802 detects a point having a high gradation value from an SEM image and extracts a center line of a pattern formed by the polymer A. Extraction of a center line is executed by, for example, removing noise from the image by using a Gauss filter or the like and then conducting binarization processing to divide the polymer A and the polymer B respectively to white and black. In addition, a center line is obtained by conducting thinning processing until a region of the polymer A (white) becomes one pixel width. It is also possible to adopt another thinning processing method.

Figure 5:
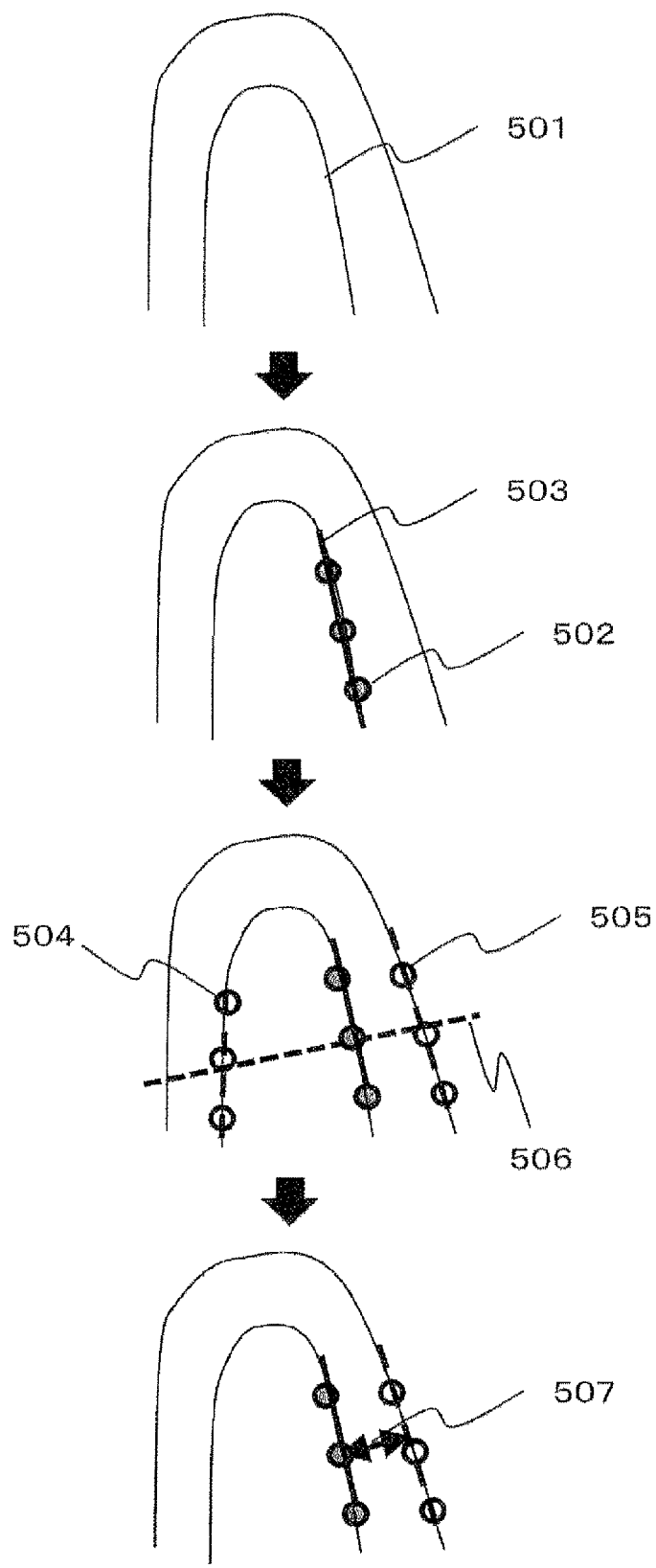
FIG. 5 is a diagram showing a process for measuring a distance between extracted center lines.

An extraction example of center lines is shown in FIG. 4(b), and a flow of measurement is shown in FIG. 5. The straight line portion extraction unit 803 arranges reference points at predetermined or arbitrary intervals along a center line 501 formed by the polymer A. And the straight line portion extraction unit 803 approximates the reference points 502 with a straight line 503, and detects center line point rows 504 and 505 of adjacent patterns caused by the polymer A intersecting a normal line 506 of the straight line 503. The straight line portion extraction unit 803 approximates a detected point row with a straight line, and compares inclination of the straight line with that of an adjacent straight line. In a case where a difference in inclination is small, the two straight lines (503, 505) are regarded as parallel. The inter-center-line dimension measurement unit 804 measures a distance 507 between the two straight line, and defines the distance 507 as pitch between two patterns. In a case where inclinations differ largely, the two straight lines (503, 504) are not parallel, and consequently measurement of the distance is not conducted.

By the way, as a technique for selectively extracting a straight line portion, for example, it is conceivable to define a segment that can be regarded as a straight line over a length of at least a predetermined value or a predetermined number of points, as a straight line and exclude a segment in which a straight line portion is less than a predetermined value or less than a predetermined number of points in length from a measurement target as other than a straight line. Furthermore, it is also possible to find a correlation coefficient between an approximate straight line and a point row at the time when straight line approximation is conducted, exclude a portion having a value of the correlation coefficient less than a preset threshold from measurement targets, and define remaining portions as straight lines (as measurement targets). Furthermore, it is also possible to find curvature of a point row, exclude a portion having curvature of at least a predetermined threshold or larger than a predetermined threshold from measurement targets, and define remaining portions as straight lines (as measurement targets).

Furthermore, in a case where a measurement target region is to be further selected from the straight line portion extracted as described above, a dimension between segments that are adjacent to each other (another segment is not included between the segments) and that have a relative angle between less than a predetermined value should be measured selectively or output.

Figure 6:
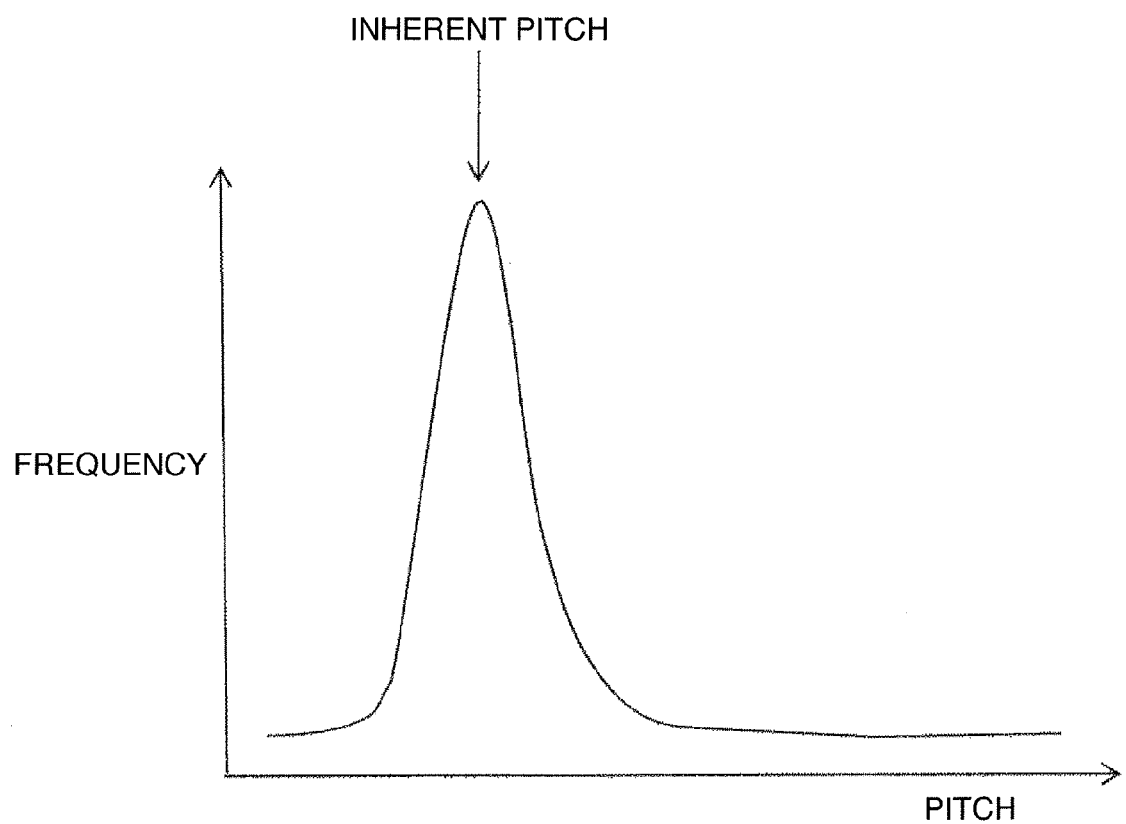
FIG. 6 is a histogram showing a relation between a distance value between center lines in a predetermined area and a frequency of regions indicating the distance value.

This measurement is conducted for the whole SEM image or a predetermined region in the SEM image, and as many measured values of the pitch as the number of point rows on the center lines are found. If the histogram creation unit 805 conducts histogram analysis on them as shown in FIG. 6, a pitch having the highest frequency can be found as the inherent pitch of the material. The measured value output unit 808 outputs a dimension between segments that belong to straight line portions and that can be regarded as parallel to an adjacent contour line, to the display device in the input device 809 or the like as a measurement result.

Even for a pattern such as the fingerprint pattern, it becomes possible to conduct the aimed measurement (pitch measurement) with high precision by making a measured value of a high frequency selectively as a measurement result in this way. By the way, in the present embodiment, an example of adopting a measured value that is the highest in frequency as a measurement result has been described. However, a measured value that has a specific frequency other than the highest frequency may be output as a measurement result according to the object.

By the way, in the above-described technique, it must be determined whether two patterns are parallel on the basis of inclination of a point row, in all detection points of pattern centers existing in the whole screen of an SEM image. Therefore, it takes long time to conduct processing in some cases. In a case where it is desired to give priority to speed up of the processing, detection points should be thinned, or it is possible to previously extract parallel portions from the SEM image and conduct pitch measurement only in that portion. In that case, it can be implemented by using an image processing technique such as the Hough transform which is generally known as straight line extraction means on a digital image.

In a case where a length or ratio of a straight line region in the finger print pattern is to be measured as well, extraction of a straight line region is possible by using a technique similar to that described above. For example, the ratio of straight line regions can be found by finding a length of portions judged to be straight lines in the sum total of lengths of center lines in the whole pattern.

The finger print pattern conducts self-assembly by annealing, and lines up as a pattern shape of a semiconductor device. Many of patterns formed on the basis of the fingerprint pattern are line patterns having a straight line shape. As for the fingerprint pattern as well, it can be said that a material including many straight line portions is a material suitable for patterning. Therefore, it becomes possible to conduct quantitative analysis of polymers applied to the DSA technique and conduct proper selection of polymers based on the quantitative analysis by finding a ratio of straight line portions. By the way, the ratio of straight line portions to whole segments included in the visual field or a predetermined region in the visual filed may be output, or the ratio of straight line portions to curved line portions may be output.

A method for measuring LER (Line Edge Roughness) of a pattern will now be described with reference to FIG. 7. FIG. 7 is a schematic diagram of an SEM image of the fingerprint pattern, and represents a fingerprint pattern including a pattern A 701 and a pattern B 702. First, it is necessary to define a line that becomes a reference of LER. As for this, a segment 703 coupling a point row on a center line can be used. If the center line-edge dimension measurement unit 807 extracts left and right edges (704, 705) of the pattern A besides the center line 703 and measures a distance 710 to an edge detection point located in a normal direction of the center line, variations of the distance 710 can be defined as the LER. Or since variations of the line width is a square sum of edge position variations respectively of edges on both sides, a distance (line width) between edge detection points located in the normal direction on both sides with the center line between is measured and variations of edges on one side is calculated from variations of the line width.

Since variations of the center line itself exert an influence upon the LER, however, it is necessary that variations of the center line are previously removed. The variations can be removed by finding a center line after the smoothing processing unit 806 smoothes an image, or by smoothing found center lines. Since the fluctuation component and roughness peculiar to the fingerprint have a great difference in frequency, a method of providing a threshold for the frequency and masking the fluctuation component and then reconstructing an image is also effective.

In the foregoing method, extraction of a straight line portion from an SEM image already acquired and evaluation have been described. However, it is also possible to search for a straight line portion from an image of low magnification acquired previously by using a similar method, re-acquire an SEM image of the straight line portion, and then conduct evaluation.

The pattern measurement technique disclosed in the present specification can be applied to an electron microscope or a charged particle beam device similar to the electron microscope as long as it is capable of acquiring an image.

REFERENCE SIGNS LIST

001: SEM
101: Electron gun
102: Electron beam
103: Condenser lens
104: Deflector
105: Object lens
106: Sample
107: Detector
108: Image processing unit
109: Arithmetic operation unit
110: Output unit

The invention claimed is:

1. A pattern measurement device that measures a pattern on a sample based on a fingerprint pattern image acquired by a charged particle beam device, comprising:
an arithmetic operation device programmed to selectively extract straight line portions of a pattern on the sample or portions which can be approximated by a straight line from within the fingerprint pattern image acquired by the charged particle beam device, and output at least one of measurement of a distance between the extracted portions, a ratio of the extracted portions in a predetermined region, and lengths of the extracted portions.

2. The pattern measurement device according to claim 1, wherein the arithmetic operation device conducts arithmetic operations as to a distance between contour lines which become centers of patterns on the sample, a ratio of straight line portions in the contour lines, and a length of a straight line portion.

3. The pattern measurement device according to claim 1, wherein the pattern on the sample is a fingerprint pattern.

4. The pattern measurement device according to claim 3, wherein the arithmetic operation device measures a distance between a center line of one pattern included in the fingerprint pattern and a center line of an adjacent pattern.

5. The pattern measurement device according to claim 3, wherein the arithmetic operation device extracts a straight line portion of a center line included in the finger print pattern and measures a length of the extracted segment.

6. The pattern measurement device according to claim 3, wherein the arithmetic operation device finds a ratio of straight line portions in a predetermined region included in the fingerprint pattern.

7. The pattern measurement device according to claim 1, wherein the arithmetic operation device compares an inclination of an approximate straight line of a point row included in the pattern center line with an inclination of an approximate straight line of an adjacent point row, determines whether the approximate lines are parallel on the basis of a difference between the inclinations, and judges portions that are long in parallel region to be straight lines.

8. The pattern measurement device according to claim 1, wherein the arithmetic operation device continuously calculates an inclination of an approximate straight line of a point row included in the pattern center line along the center line, and judges a portion where a change of inclination is small to be a straight line.

9. The pattern measurement device according to claim 1, wherein the arithmetic operation device finds a radius of curvature per unit length of an approximate curve of a point row included in the pattern center line, and judged a portion having a small radius of curvature to be a straight line.

10. The pattern measurement device according to claim 1, wherein the arithmetic operation device finds a frequency for every measurement result of the distance between the extracted portions, and outputs a measurement result of a specific frequency as the distance between the extracted portions.

11. The pattern measurement device according to claim 10, wherein the arithmetic operation device outputs a measurement result of a largest frequency as the distance between the extracted portions.

12. The pattern measurement device according to claim 1, wherein the pattern on the sample is formed by microlayer separation in a block copolymer including a plurality of polymers.

13. A pattern evaluation method for evaluating a polymer used in self-assembly lithography, comprising:
selectively extracting straight line portions of patterns or portions that can be approximated with a straight line from within a fingerprint pattern image obtained by a charged particle beam device; and
finding at least one of measurement of a distance between the extracted portions, a ratio of the extracted portions in a predetermined region, and lengths of the extracted portions.

14. A non-transitory computer-readable medium encoded with computer program instructions, which when executed by a processor, cause the processor to measure a pattern on a sample based on an image acquired by a charged particle beam, the computer program instructions causing the processor to:
selectively extract straight line portions of patterns or portions that can be approximated with a straight line from within a fingerprint pattern image obtained by a charged particle beam device; and
find at least one of measurement of a distance between the extracted portions, a ratio of the extracted portions in a predetermined region, and lengths of the extracted portions.

15. A pattern measurement device including an arithmetic operation device that measures a fingerprint pattern arranged with random directionality in a fingerprint form, by using a signal obtained on the basis of scanning on a sample with a charged particle beam, the arithmetic operation device extracting a center line and both left and right edges of the fingerprint pattern from a signal obtained on the basis of scanning with the charged particle beam line; and the arithmetic operation device calculates a feature quantity of the fingerprint pattern on the basis of a position relation between the center line and both the left and right edges.

16. The pattern measurement device according to claim 15, wherein the fingerprint pattern is formed by micro phase separation in a block copolymer including two kinds of polymer.

17. The pattern measurement device according to claim 15, wherein the arithmetic operation device finds variations of distances between the center line of the pattern and the left and right edges.

* * * * *